(12) United States Patent
Chang

(10) Patent No.: US 9,408,411 B1
(45) Date of Patent: Aug. 9, 2016

(54) BACTERIOSTATIC MOULD-PROOF ANTISEPTIC PASTER

(71) Applicant: Wei-Yin Chang, Taichung (TW)

(72) Inventor: Wei-Yin Chang, Taichung (TW)

( * ) Notice: Subject to any disclaimer, the term of this patent is extended or adjusted under 35 U.S.C. 154(b) by 0 days.

(21) Appl. No.: 14/808,199

(22) Filed: Jul. 24, 2015

(51) Int. Cl.
| | |
|---|---|
| A23L 3/3454 | (2006.01) |
| B32B 7/12 | (2006.01) |
| B32B 27/10 | (2006.01) |
| B32B 27/30 | (2006.01) |
| B32B 27/36 | (2006.01) |
| B32B 29/00 | (2006.01) |
| A61L 2/232 | (2006.01) |
| A01N 25/34 | (2006.01) |

(52) U.S. Cl.
CPC .............. *A23L 3/3454* (2013.01); *A61L 2/232* (2013.01); *B32B 7/12* (2013.01); *B32B 27/10* (2013.01); *B32B 27/30* (2013.01); *B32B 27/36* (2013.01); *B32B 29/002* (2013.01); *B32B 29/005* (2013.01); *A01N 25/34* (2013.01); *A23V 2002/00* (2013.01); *B32B 2255/12* (2013.01); *B32B 2437/02* (2013.01)

(58) Field of Classification Search
CPC ........ A01N 25/34; B32B 27/10; B32B 27/30; B32B 27/36
See application file for complete search history.

(56) References Cited

U.S. PATENT DOCUMENTS

| | | | |
|---|---|---|---|
| 5,246,663 A * | 9/1993 | Ohama ................... | A01N 47/46 220/87.1 |
| 5,417,974 A * | 5/1995 | Sekiyama ............... | A01N 25/18 424/405 |
| 2010/0255049 A1 * | 10/2010 | Chang .................... | A01N 25/34 424/414 |

* cited by examiner

*Primary Examiner* — Betelhem Shewareged
(74) *Attorney, Agent, or Firm* — Rosenberg, Klein & Lee

(57) ABSTRACT

This Invention is with respect to a kind of bacteriostatic mold-proof antiseptic paster, which is mainly composed of forming a graphic layer on a base material after printing, and the upward side of the graphic layer fitting for a lustering film polyester layer, which is a implastic viscose with a lustering layer, and there is a lower PE lamination layer below the base material, and a release lamination layer below the lower PE lamination layer. In this way, it forms a sheet, and then put the sheet in the fumigating tank with special raw materials to extract the edible mold-proof bacteriostatic material, to constitute a bacteriostatic mold-proof antiseptic paster.

1 Claim, 3 Drawing Sheets

BACTERIOSTATIC MOULD-PROOF ANTISEPTIC PASTER

BACKGROUND OF THE INVENTION a) Field of the Invention

This Invention is related to a kind of bacteriostatic mould-proof antiseptic paster, especially a kind of bacteriostatic mould-proof antiseptic paster which is damp-proof and no easy to deformation. It could be used as common food bacteriostatic mould-proof piece, and also put directly in the shoes for bacteriostasis and deodorization.

b) Description of the Prior Art

According to the habitual use to keep the food or food material fresh and avoid the damp and mouldy, it usually puts the chemicals as desiccant bag or deoxidation bag in, to realize the mould-proof effect. However, the aforesaid chemicals are more or less no good for human health, thus the industry researched and developed a kind of mould-proof paster made in the gasification mode, as Certificate No. TWM 290754 "Mould-proof Paster", which mainly contains a release paper and a paster, and the paster contains the volatilizable mould-proof composition, to realize the effect of easy to use through the paster and release paper separated and pasted in the vessel; but the mould-proof component is still the chemical, therefore, in this project, the Inventor researched and developed the Publication No. TW201034586 (A) "Environmental-protection Bacteriostatic Mould-proof Antiseptic Paster".

The Publication No. TW201034586 (A) "Environmental-protection Bacteriostatic Mould-proof Antiseptic Paster" adopts a kind of natural material as the mould-proof material, to effectively solve the above said deficiency, and achieve the relatively great reflection. However, the Inventor found that the bacteriostatic mould-proof antiseptic paster could not only be used for common food material, but also put directly in the shoes or cabinet, to realize the bacteriostatic mould-proof effect; but when used in the shoes, since the feet contact with the bacteriostatic mould-proof paster, if there is sweat, it is easy to cause the bacteriostatic mould-proof paster gets wet and curl, and then affects the comfort of wearing shoes.

SUMMARY OF THE INVENTION

In view of the above reasons, the Inventor continuously researches and improves, and develops a kind of paster able to use for both common food material and put in the shoes for bacteriostatic mould-proof and deodorization, which is mainly made by a base material after printing to form a graphic layer, and the graphic layer fits for a lustering film polyester layer through a process machine, while there is a lower PE lamination layer and release lamination layer below the base material, and in this way there forms a sheet, then the sheet is put in the fumigating tank with special raw materials to extract the edible mould-proof bacteriostatic material; after the fumigation and penetration procedure in the chamber, to make the sheet absorbing the extracted edible mould-proof bacteriostatic material, and form a bacteriostatic mould-proof antiseptic paster; through the lustering film polyester layer, lower PE lamination layer, and release lamination layer, to wrap the base material, and make the base material releasing slowly in stable amount; and for the lower PE lamination layer and release lamination layer, the bacteriostatic mould-proof paster is not easy to be wet and deformed, and destroy the paper structure, thus applicable to be used in the shoes directly.

DETAILED DESCRIPTION OF THE INVENTION

Figure 1:
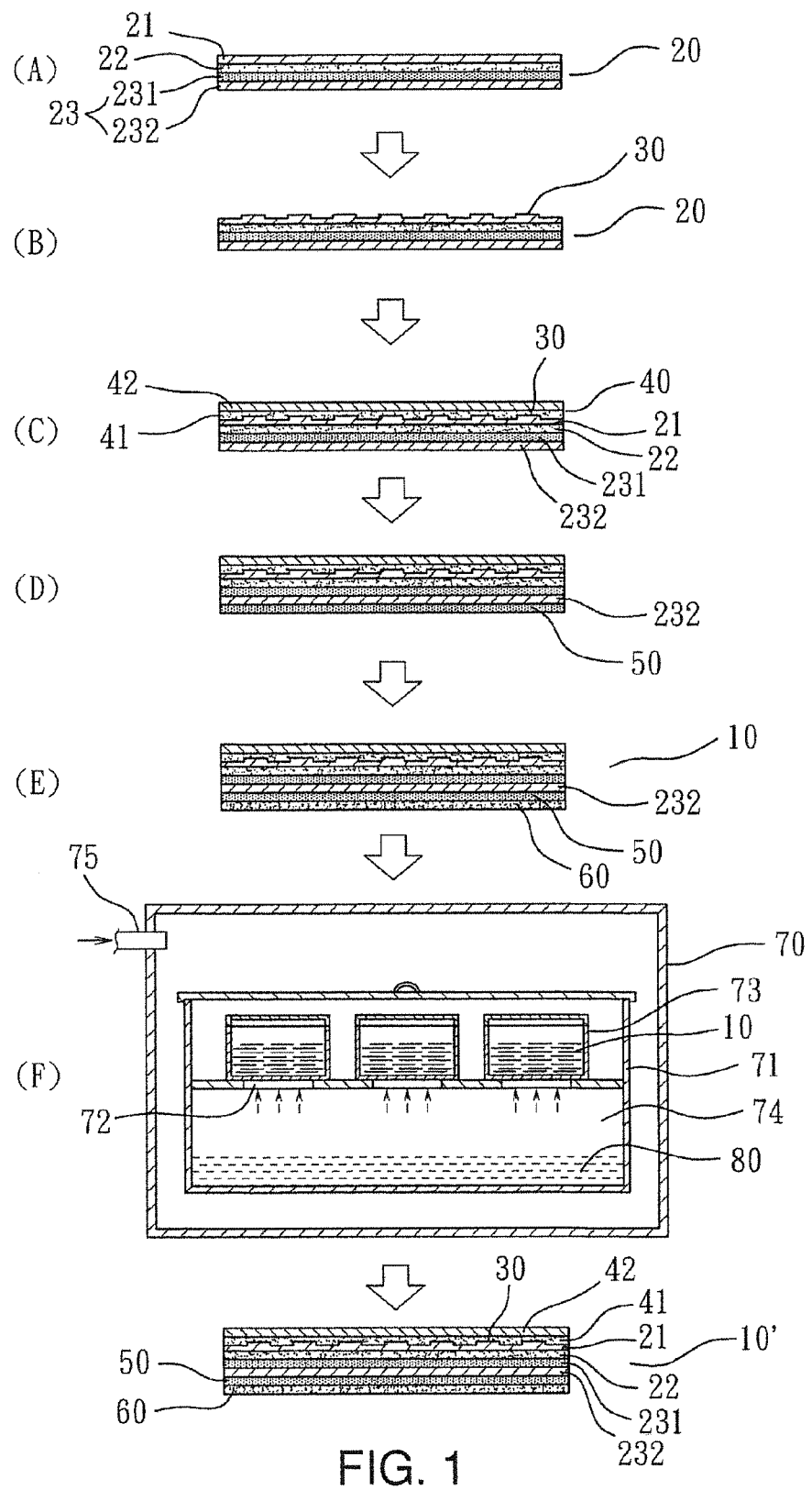
FIG. 1 is the schematic diagram of manufacturing flow of the present invention.
Figure 2:
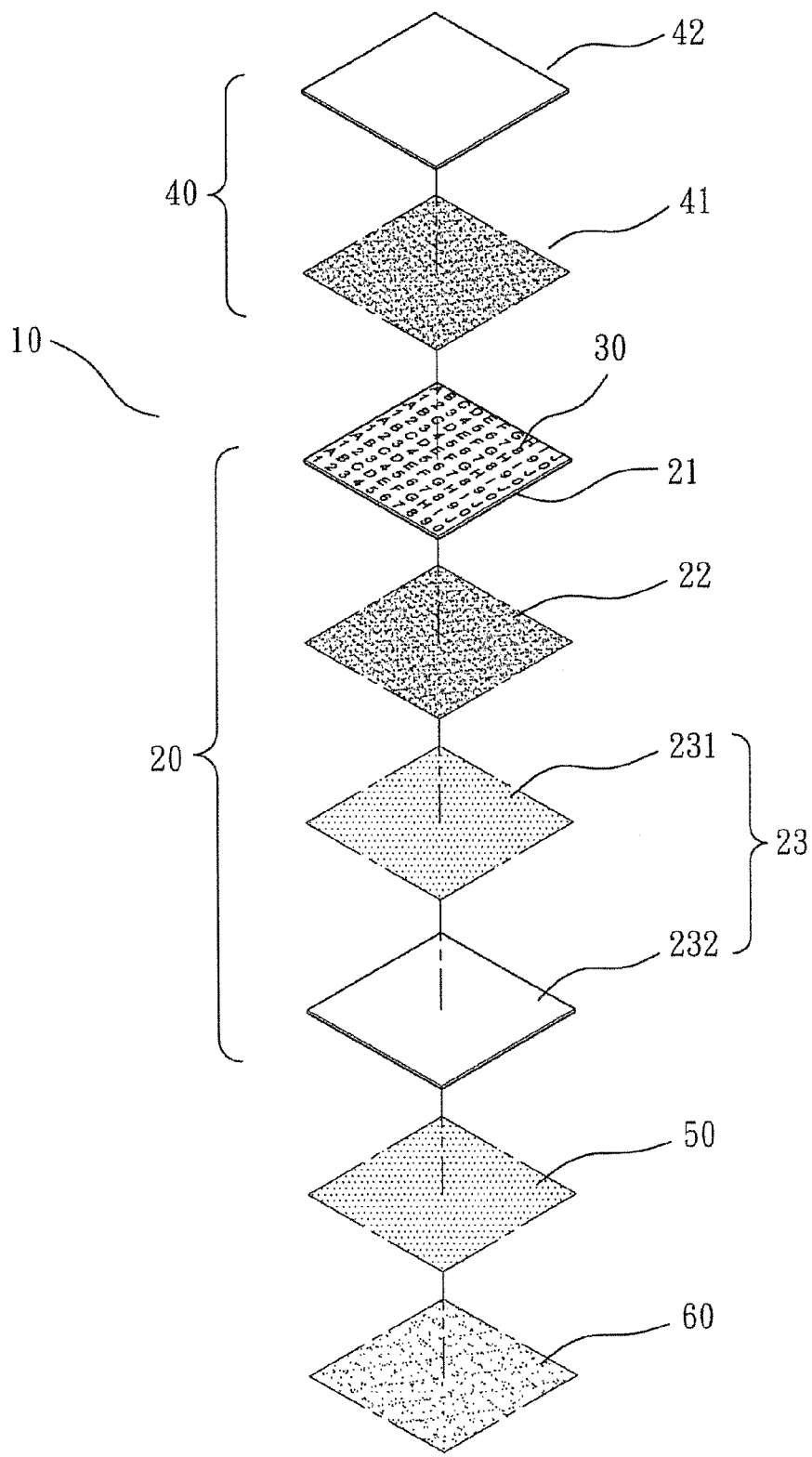
FIG. 2 is the schematic diagram of structural decomposition of the present invention.
Figure 3:
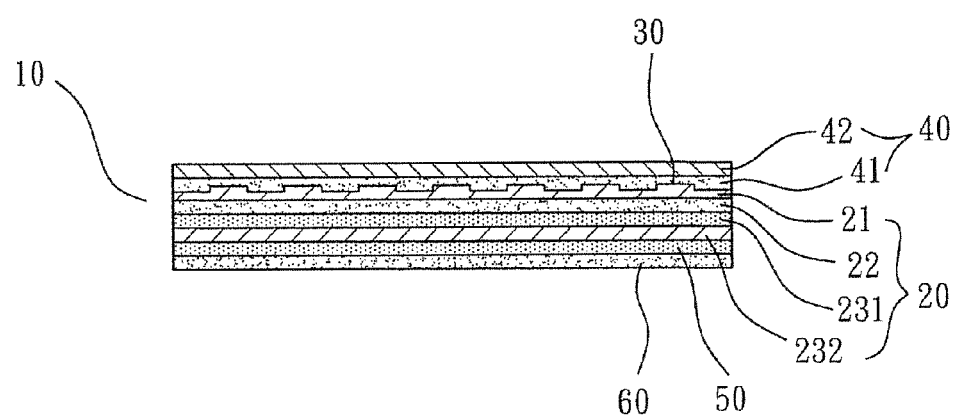
FIG. 3 is the section view of structure of the present invention.

Please refer to FIG. 1 to FIG. 3, this Invention mainly includes:

(A) Base material 20: consists of a upper backing paper (coated paper) 21, a water-based adhesive layer 22 below and a lower backing paper 23, and the lower backing paper 23 is a glassine 232 with a PE lamination layer 231;

(B) Printing graphic layer 30: is the graphic layer 30 with printed script or pattern on the base material 20;

(C) Lustering film polyester layer 40: is above the base material 20, using process machine to fit for the base material 20, and the lustering film polyester layer 40 is a implastic viscose 41 with a lustering layer 42;

(D) Lower PE lamination layer 50: is sprayed on the base material 20 below the glassine 232, which has good waterproof and heat-proof features;

(E) Release lamination layer 60: is sprayed below the lower PE lamination layer 50, with the character of level and uneasy to get wet and deformed, to form the sheet 10;

(F) Fumigation and penetration procedure in the chamber: is to put the sheet 10 in the steam box 73, and place the steam box 73 above the thru hole 72 of fumigator 71; the fumigator 71 is put in a chamber 70, and the chamber 70 is heated by the thermostat controller 75 and maintain the internal temperature within 25° C.-50° C.; the bottom of fumigator 71 is a fumigating tank 74; the fumigating tank 74 is injected to extract the special edible mould-proof bacteriostatic raw material 80, to fumigate the sheet 10 for fifty to seventy hours, for the saturated absorption of the special extracted edible mould-proof bacteriostatic raw material 80 (the component of the special extracted edible mould-proof bacteriostatic raw material is the existing technology, such as: allyl isothiocyanates, and thus not described in details hereby);

(G) Mould-proof finished product: the finished product of bacteriostatic antiseptic paster 10 with mould-proof effect.

In this way, it replaces the chemical through the natural special extracted edible mould-proof bacteriostatic component, to achieve the environmental protection effect, and realize the saturated absorption of special extracted edible mould-proof bacteriostatic component through the fumigation and penetration procedure in the chamber, to greatly improve the mould-proof bacteriostatic effect and extend the mould-proof time period; at the same time, for the lustering film polyester layer 40, lower PE lamination layer 50 and release lamination layer 60, it wraps the base material to slowly release the mould-proof component in stable amount, to realize the double extension of mould-proof bacteriostatic and fresh time period; moreover, the base material could be torn off from the lower backing paper 23 after used to identify the mould-proof component amount, and delay the food material turning yellow; additionally, the lower PE lamination layer 50 has good waterproof and heat-proof features, while the release lamination layer 60 is with the character of level and uneasy to get wet and deformed, which ensure when this Invention is placed in the shoes, it shall not be wet and curl for sweat, to both realize the bacteriostatic effect, and not affect the comfort of wearing shoes.

Furthermore, when the bacteriostatic mould-proof antiseptic paster of this Invention is thick, it could increase the mould-proof component amount as well as extending the mould-proof bacteriostatic time period; on the contrary, when the bacteriostatic mould-proof antiseptic paster is thin, for the lower PE lamination layer 50 and release lamination layer 60, it shall not stick on the feet to make uncomfortable when putting in the shoes.

What is claimed is:

1. A kind of bacteriostatic mould-proof antiseptic paster, is mainly composed of forming a graphic layer on a base material after printing, and the upward side of the graphic layer fitting for a lustering film polyester layer, which is an implastic viscose with a lustering layer, and there is a lower PE lamination layer below the base material, and a release lamination layer below the lower PE lamination layer so as to form a sheet, and then put the sheet in the fumigating tank with special raw materials to extract the edible mould-proof bacteriostatic material; after the fumigation and penetration procedure in the chamber, the sheet shall absorb the special extracted edible mould-proof bacteriostatic raw material, whose manufacturing flow includes:

Base material: consists of a upper backing paper, a water-based adhesive layer below and a lower backing paper, and the lower backing paper is a glassine with a PE lamination layer;

Printing graphic layer: is the graphic layer with printed script or pattern on the base material;

Lustering film polyester layer: is above the base material, using process machine to fit for the base material, and the lustering film polyester layer is a implastic viscose with a lustering layer;

Lower PE lamination layer: is sprayed on the base material below the glassine, which has good waterproof and heat-proof features;

Release lamination layer: is sprayed below the lower PE lamination layer, with the character of level and uneasy to get wet and deformed, to form a sheet;

Fumigation and penetration procedure in the chamber: is to put the sheet in the steam box, and place the steam box above the thru hole of fumigator; the fumigator is put in a chamber, and the chamber is heated by the thermostat controller and maintain the internal temperature within 25° C.-50° C.; the bottom of fumigator is a fumigating tank; the fumigating tank is injected to extract the special edible mould-proof bacteriostatic raw material, to fumigate the sheet for fifty to seventy hours, for the saturated absorption of the special extracted edible mould-proof bacteriostatic raw material component;

Mould-proof finished product: the finished product of bacteriostatic antiseptic paster with mould-proof effect.

\* \* \* \* \*